United States Patent
Van Den Ende et al.

(10) Patent No.: US 12,193,824 B2
(45) Date of Patent: Jan. 14, 2025

(54) METHOD AND SYSTEM FOR OBTAINING SIGNALS FROM DRY EEG ELECTRODES

(71) Applicant: KONINKLIJKE PHILIPS N.V., Eindhoven (NL)

(72) Inventors: Daan Anton Van Den Ende, Breda (NL); Sander Theodoor Pastoor, Vleuten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1046 days.

(21) Appl. No.: 16/019,659

(22) Filed: Jun. 27, 2018

(65) Prior Publication Data
US 2019/0000338 A1     Jan. 3, 2019

Related U.S. Application Data

(60) Provisional application No. 62/525,926, filed on Jun. 28, 2017.

(30) Foreign Application Priority Data

Aug. 22, 2017    (EP) ..................................... 17187362

(51) Int. Cl.
    *A61B 5/291*     (2021.01)
    *A61B 5/00*     (2006.01)
    *A61B 5/0531*     (2021.01)

(52) U.S. Cl.
    CPC ............ *A61B 5/291* (2021.01); *A61B 5/0531* (2013.01); *A61B 5/6814* (2013.01); *A61B 5/6843* (2013.01)

(58) Field of Classification Search
CPC ...... A61B 5/0478; A61B 5/6843–6844; A61B 5/0531; A61B 5/369
See application file for complete search history.

(56) References Cited

U.S. PATENT DOCUMENTS

| | | |
|---|---|---|
| 2011/0015503 A1 | 1/2011 | Joffe et al. |
| 2011/0015942 A1* | 1/2011 | Oakley ................. G16H 50/20 705/2 |

(Continued)

FOREIGN PATENT DOCUMENTS

| | | |
|---|---|---|
| EP | 3135191 A1 | 3/2017 |
| WO | 2011055291 A1 | 5/2011 |
| WO | 2013038285 A1 | 3/2013 |

OTHER PUBLICATIONS

"Flex Sensors", Cognionics, inc., San Diego, CA, Accessed Jun. 27, 2018, https://www.cognionics.net/flex-sensors.

(Continued)

*Primary Examiner* — Rene T Towa
*Assistant Examiner* — Huong Q Nguyen
(74) *Attorney, Agent, or Firm* — Michael W. Haas

(57) ABSTRACT

An electroencephalography (EEG) system includes a support configured to be positioned at least partially around the head of a user, an EEG electrode configured to be supported by the support and to be positioned for contacting skin of the user, an actuator operatively coupled to the EEG electrode and configured to move the electrode in at least two dimensions, including an axial dimension and a lateral dimension to enable the EEG electrode to contact the skin at different locations, and one or more physical processors operatively connected with the EEG electrode and the actuator. The one or more physical processors being programmed with computer program instructions which, when executed cause the one or more physical processors to: obtain an impedance signal from the EEG electrode; and actuate the actuator to move the EEG electrode based on a comparison of the obtained impedance signal with an impedance threshold.

11 Claims, 7 Drawing Sheets

(56) References Cited

U.S. PATENT DOCUMENTS

| | | | |
|---|---|---|---|
| 2011/0237923 A1* | 9/2011 | Picht | A61B 5/6843 |
| | | | 600/383 |
| 2012/0143020 A1 | 6/2012 | Bordoley et al. | |
| 2014/0051044 A1* | 2/2014 | Badower | A61B 5/291 |
| | | | 434/236 |
| 2015/0282760 A1 | 10/2015 | Badower et al. | |
| 2016/0143554 A1* | 5/2016 | Lim | A61B 5/6814 |
| | | | 600/383 |
| 2017/0055903 A1* | 3/2017 | Cramer | A61B 5/6831 |
| 2017/0112444 A1 | 4/2017 | Lin et al. | |

OTHER PUBLICATIONS

"Mobile EEG Solutions", Cogniotics, Inc., San Diego, CA, Accessed Jun. 27, 2018, https://www.cognionics.net/.

* cited by examiner

Electrode P3 has bad contact quality

METHOD AND SYSTEM FOR OBTAINING SIGNALS FROM DRY EEG ELECTRODES

CROSS-REFERENCE TO PRIOR APPLICATIONS

This application claims the benefit of U.S. Provisional Application No. 62/525,926, filed 28 Jun. 2017 and European Patent Application No. 17187362.3, filed on 22 Aug. 2017. This application is hereby incorporated by reference herein.

BACKGROUND

1. Field

The present disclosure pertains to a method and a system for measuring electrical brain activity, also known as electroencephalography (EEG) or the measurement of an electroencephalogram. Specifically, the present disclosure pertains to a method and a system for obtaining signals from one or more dry EEG electrodes of an EEG system.

2. Description of the Related Art

EEG measures the brain's activity electrically and is a non-invasive neurological monitoring tool that is gaining momentum both in professional healthcare and consumer home health applications. For example, the EEG recordings or measurements are being used for many clinical applications including epilepsy prediction, diagnosis of sleep disorders, biofeedback therapy and recently even neuromarketing.

Electrical brain activity or EEG is generally measured by means of EEG electrodes contacting skin of the user, in particular the scalp of the user. One type of known electrodes is wet or gel electrodes. And another type of known electrodes is dry electrodes (not using gel).

For the EEG recording applications, it is desired to have low galvanic impedance with the skin of the user in order to have good signal quality. For applications such as daily sleep monitoring or continuous epilepsy monitoring treatment, it is also important to have an easy to use electrode. For good EEG recordings, multiple positions have to be monitored simultaneously and electrodes have to be applied to the head, including those areas covered by hair. The quality of the electrical connection is limited especially for people with thick hair.

The main challenge, when applying the wet or gel EEG electrodes, is to get a good, thus low, contact impedance to the skin of the user. In clinical measurements, this is normally done with a (shower-cap like) rubber cap with integrated metal electrodes (e.g., Ag/AgCl coated). The skin underneath these wet or gel EEG electrodes usually needs to be prepared by decreasing and often additional abrasion (e.g., removal of the dry top layer of the skin, the stratum corneum). The conductive paste or gel is then applied between each electrode and the scalp (typically through a hole in the electrode or cap).

Cup electrodes filled with conductive paste are also traditionally used for EEG monitoring. Cup electrodes filled with conductive paste are known for the low impedance due its composition. Conductive paste enables adhesiveness and conductivity and contacts the skin through the subject's hair. This assures a low ohmic contact to the deeper skin layer (the epidermis) and "conversion" from ion current in the body to electron current in the measuring system. The use of the conductive paste also solves (partly) the problem of the varying distance between the electrode and the user's skin due to the variation from person to person with respect to the hair layer thickness and the amount of hair, as well as temporal changes of the distance that may occur due to the head and/or body motion.

However, in a lot of cases not involving clinical measurements (i.e., outside clinical applications), for example, for lifestyle consumer products, for disabled patients or for remote monitoring applications/purposes, these kinds of wet or gel electrodes are not practical. For example, these wet electrodes are generally very cumbersome to set up and typically only suitable in clinical environments, not for continuous measurements by the user. Also, these wet electrodes are for a single use and limited durability for continuous measurements. These wet electrodes also dry out in a few hours, are not easy for attachment to body and device. Also, the conductive paste applied between each electrode and the scalp leaves a lot of paste residuals after use. These all together make the wet or gel EEG electrodes not very suitable for daily long term use at home for medical or consumer health applications.

FIG. 1 shows a fully dry EEG electrode headset. For instance, Imec NL (Holst) has developed a headset using dry EEG electrodes. Commercially available dry headsets are provided by Cognionics. Dry electrodes have partially overcome some of the above-discussed problems by applying a pin-like structure that has the ability to bypass the hairs on the scalp. However, in practice, when these solutions are applied to a larger population, there are still difficulties letting sufficient signal quality especially when coping with thick and/or long hair. A problem with these solutions can be a poor contact to the skin (or the scalp) and insufficient signal quality. The dry electrodes hardly achieve the signal quality and good electrical connection (low impedance) which can be achieved with the wet or hydrogel electrodes. These dry EEG electrodes are still very sensitive to making good contact. This must be corrected by hand (i.e., by a trained supervisor in clinical environment) and will amount in extra setting up time. In a less controlled environment, the incorrect placement can also lead to loss of data.

Although the dry electrodes are easier to apply, they are more sensitive to movement and (intermittent) loss of contact. Short interruptions are typically not harmful in continuous monitoring. Most designs use springs to apply pressure to limit the movement of the dry electrodes when the whole dry EEG headset moves. For small movements of the EEG headset, this spring loaded electrode approach is helpful. However, for larger (head) movements of the EEG headset, the spring loaded electrode approach has limited success. More importantly, the movements of the EEG headset may lead to a different new contact state, possibly leading to poor contact by blocking hairs in between the electrode and the skin. Especially, the large movements of the EEG headset can cause temporary release of the dry EEG electrode from the skin, so the user's hair can come between the electrode surface and the skin. In practice, especially, when the dry EEG headset consists of multiple dry EEG electrodes, there is a large chance that at least one of the dry EEG electrodes is malfunctioning. FIG. 2 shows a graph of electrode impedance values at several electrode positions over time from the dry EEG electrode headset such as shown in FIG. 1. Referring to FIG. 2, channel 4 (purple) behaves in opposite fashion to channel 1 (blue).

Currently, the commercial dry electrode system with the ability to penetrate hair by actuation is the Cognionics flex system which, by design moves the contact pins of the sensor across the skin when pressed (http://www.cognionics.com/index.php/products/sensors/flex). Such a system has less chance of being blocked by hairs. However, this is still a single shot approach and needs manual adjustment when the first attempt is not adequate and the problem for multiple sensor systems is not solved.

International Patent Application No. WO2013038285A1 discloses a method to improve the signals of multi-electrode EEG headset. The method discloses a pressure control system and uses impedance measurements, pressure sensors and actuators to control the axial pressure (i.e., perpendicular to the scalp) of the electrode(s). It also describes how the impedance measurements can be used to determine the quality of contact between the individual electrodes and how to adjust the axial pressure of the electrode(s) if differences in the electrode's signal quality are observed.

The present patent application discloses improvements over the prior art systems.

SUMMARY

Accordingly, it is an object of one or more embodiments of the present patent application to provide an Electroencephalography (EEG) system. The EEG system includes a support configured to be positioned at least partially around the head of a user, an EEG electrode configured to be supported by support and to be positioned for contacting skin of the user, an actuator operatively coupled to the EEG electrode, and one or more physical processors. The actuator is configured to move the EEG electrode in at least two dimensions, including an axial dimension and a lateral dimension to enable EEG electrode to contact the skin at different locations. The one or more physical processors are operatively connected with the EEG electrode and the actuator. The one or more physical processors are programmed with computer program instructions which, when executed cause the one or more physical processors to: obtain an impedance signal from the EEG electrode; and actuate the actuator to move the EEG electrode based on a comparison of the obtained impedance signal with an impedance threshold.

It is yet another aspect of one or more embodiments of the present patent application to provide a method for obtaining signals from one or more dry electroencephalography (EEG) electrodes. The method is implemented by a computer system that comprises one or more physical processors executing computer program instructions which, when executed, perform the method. The method comprises obtaining, from an electrode, impedance signal information; and actuating, by the computer system, an actuator to move the electrode in at least two dimensions, including an axial dimension and a lateral dimension to enable the electrode to contact the skin at different locations based on a comparison of the obtained impedance signal information with an impedance threshold. The electrode is configured to be positioned for contacting skin of a user. The electrode and the actuator are operatively connected with the computer system.

It is yet another aspect of one or more embodiments to provide a system for obtaining electroencephalography (EEG) signals comprising electrode means for contacting the skin of the user; means for supporting the electrode means on the head of a user; means for moving the electrode means in at least two dimensions, including an axial dimension and a lateral dimension to enable electrode means to contact the skin at different locations; means for executing machine-readable instructions with at least one processor, wherein the machine-readable instructions comprising: obtaining, from the electrode means, impedance signal information, the electrode means being configured to be positioned for contacting skin of the user; and actuating the means for moving to move the electrode means in at least two dimensions, including an axial dimension and a lateral dimension to enable the electrode to contact the skin at different locations based on a comparison of the obtained impedance signal information with an impedance threshold. The electrode means and the means for moving being operatively connected with the means for executing.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
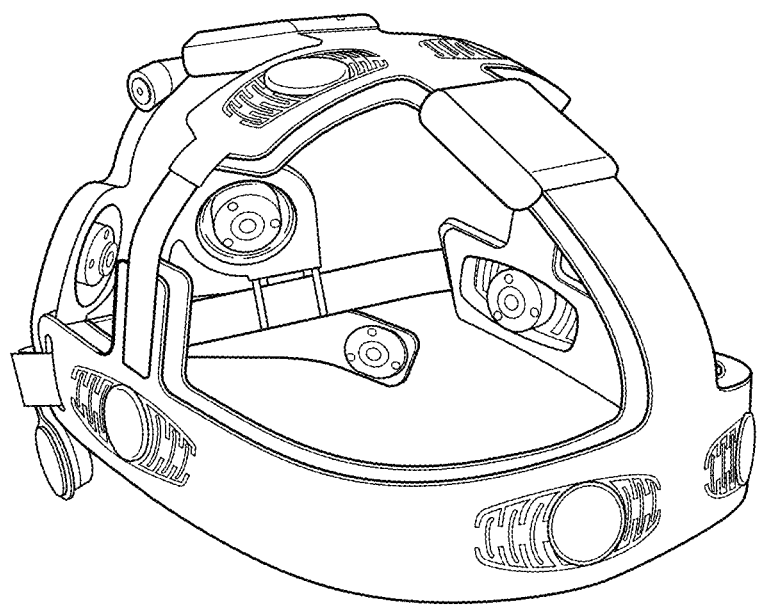
FIG. 1 is a prior art headset with dry EEG electrodes.
Figure 2:
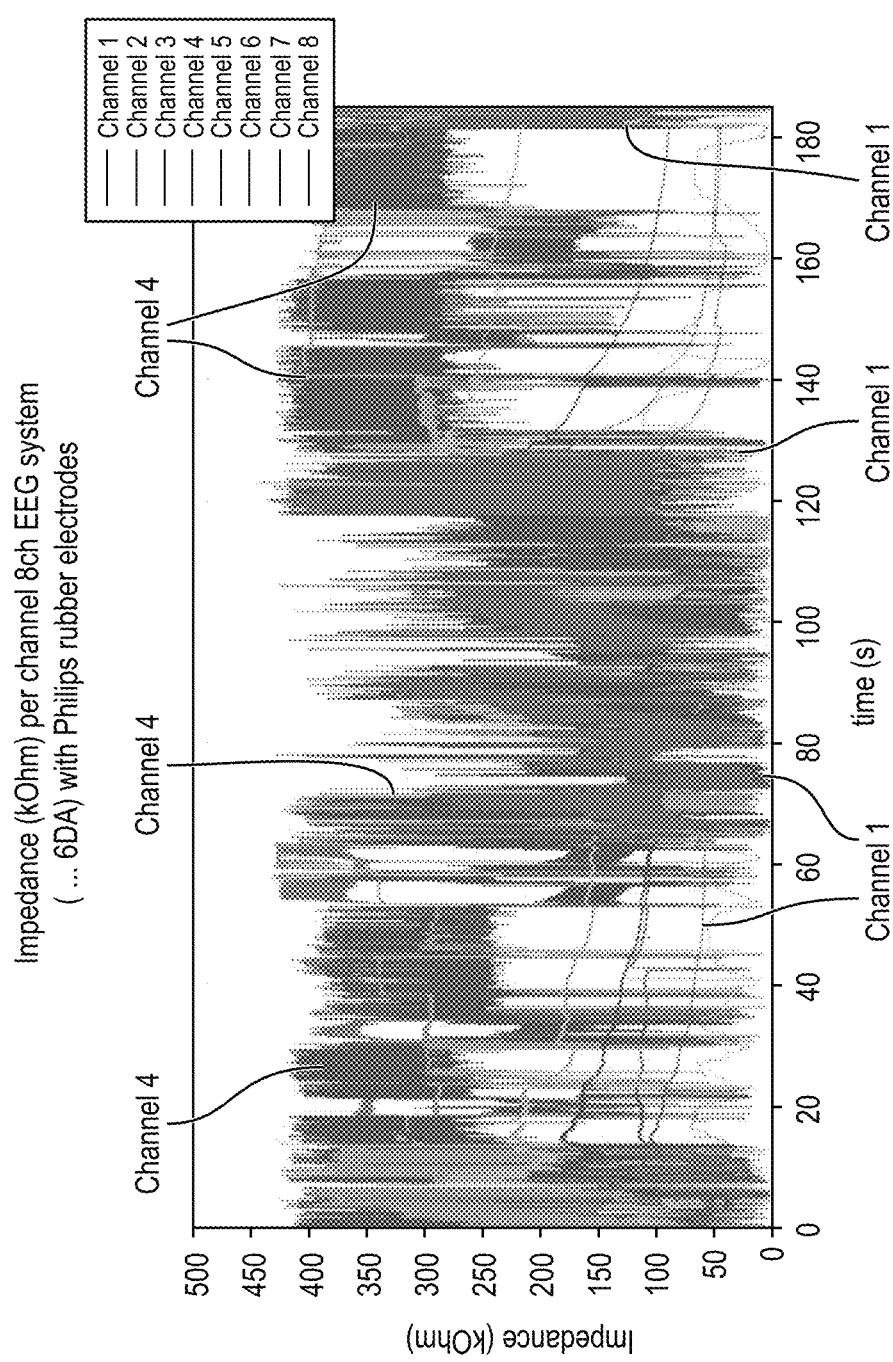
FIG. 2 shows a graph of electrode impedance values at several electrode positions over time from the dry EEG electrode headset such as shown in FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled"

means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In one embodiment, an electroencephalography (EEG) system 100 includes a support 102 configured to be positioned at least partially around the head of a user, an EEG electrode 104 configured to be supported by support 102 and to be positioned for contacting skin of the user, and an actuator 106 operatively coupled to EEG electrode 104. Actuator 106 is configured to move EEG electrode 104 in at least two dimensions, including an axial dimension and a lateral dimension to enable EEG electrode 104 to contact the skin at different locations. System 100 also includes one or more physical processors 108 operatively connected with EEG electrode 104 and actuator 106. One or more physical processors 108 are programmed with computer program instructions which, when executed cause one or more physical processors 108 to: obtain an impedance signal from EEG electrode 104, and actuate actuator 106 to move EEG electrode 104 based on a comparison of the obtained impedance signal with an impedance threshold.

In one embodiment, the present patent application provides a self-regulating solution for incorrect or sub-optimal placement of dry EEG electrode 104 of a dry EEG electrode headset 121. To avoid the above-mentioned problems associated with readjusting entire dry EEG headset 121 manually, each individual dry EEG electrode 104 on headset 121 is fitted with actuator 106. Dry EEG electrode 104 that is not performing well enough is automatically repositioned by actuation of its associated actuator 106 so as to provide a better contact of that dry EEG electrode 104 with the user's skin/scalp.

In one embodiment, the different locations include various different locations that EEG electrode 104 can be positioned to be in good contact with the user's skin. In one embodiment, these locations may also be referred to as contact positions or locations. In one embodiment, EEG electrode 104 may be positioned in a first location, a second location, a third location, and so on. Each of these first, second, and third locations being different, along the lateral dimension of the EEG electrode, from the other of the first, second, and third locations. In one embodiment, the number of different locations that EEG electrode 104 can be positioned to be in contact with the user's skin may vary.

In one embodiment, the axial dimension refers to a dimension that extends along a plane that is perpendicular to the user's scalp. In one embodiment, the axial dimension is perpendicular to the lateral dimension.

In one embodiment, the lateral dimension refers to a dimension that extends along a plane that is generally parallel to the user's scalp. In one embodiment, the lateral dimension is perpendicular to the axial dimension. In one embodiment, the lateral dimension may include two dimensions that extend along the plane that is generally parallel to the user's scalp. In one embodiment, the two dimensions are each perpendicular to the axial dimension. In one embodiment, the two dimensions extend in the same plane and are perpendicular to each other.

In one embodiment, the impedance threshold refers to a contact impedance value between electrode 104 and the person's scalp below which a sufficient EEG signal quality of dry electrode 104 is obtained. In one embodiment, actuator 106 is configured to move EEG electrode 104 such that the obtained impedance signal falls within an impedance range.

In one embodiment, the impedance range and/or threshold may be obtained by testing. In one embodiment, the impedance range and/or threshold may be obtained using data analytics. In one embodiment, the impedance range and/or threshold may be obtained from research publications.

In one embodiment, to obtain sufficient EEG signal quality using dry electrodes for real life applications, the contact impedance between electrode 104 and the person's scalp should stay below a certain value (e.g., from 1 M$\Omega$ to 10 M$\Omega$), depending on the EEG phenomena used in an application. In one embodiment, the values of the impedance range and/or threshold as described here, are up to 5 percent greater than or up to 5 percent less than those described above. In one embodiment, the values of the impedance range and/or threshold as described here, are up to 10 percent greater than or up to 10 percent less than those described above. In one embodiment, the values of the impedance range and/or threshold as described here, are up to 20 percent greater than or up to 20 percent less than those described above.

In one embodiment, a subsystem of system 100 may be configured to determine the impedance range and/or threshold using previously obtained impedance value information from a plurality of headsets. In one embodiment, this subsystem is also configured to continuously obtain subsequent impedance value information of the plurality of headsets. That is, the subsystem may continuously obtain subsequent impedance value information associated with the multiple users and/or their headsets. As an example, the subsequent information may comprise additional information corresponding to a subsequent time (after a time corresponding to information that was used to determine the signal quality). The subsequent information may be utilized to further update or modify the impedance range and/or threshold (e.g., new information may be used to dynamically update or modify the impedance range and/or threshold), etc. In one embodiment, this subsystem is configured to then continuously modify or update the impedance range and/or threshold based on the subsequent impedance value information or other subsequent information.

In one embodiment, the impedance range and/or threshold may be saved into a database (e.g., database 132 in FIG. 6) and retrieved from the database as needed. As described above, the subsystem of system 100 may continuously update/modify the impedance range and/or threshold.

As will be clear from the discussions below, in one embodiment, system 100 includes a computer system 108 that has one or more physical processors 108 programmed with computer program instructions which, when executed cause computer system and/or one or more physical processors 108 to obtain impedance signal information from one or more electrodes 104. In one embodiment, system 100 may include an adaptive feed-forward compensation/control and/or a feed back compensation/control to continuously to move EEG electrode 104 via its associated actuator 106.

Figure 3:
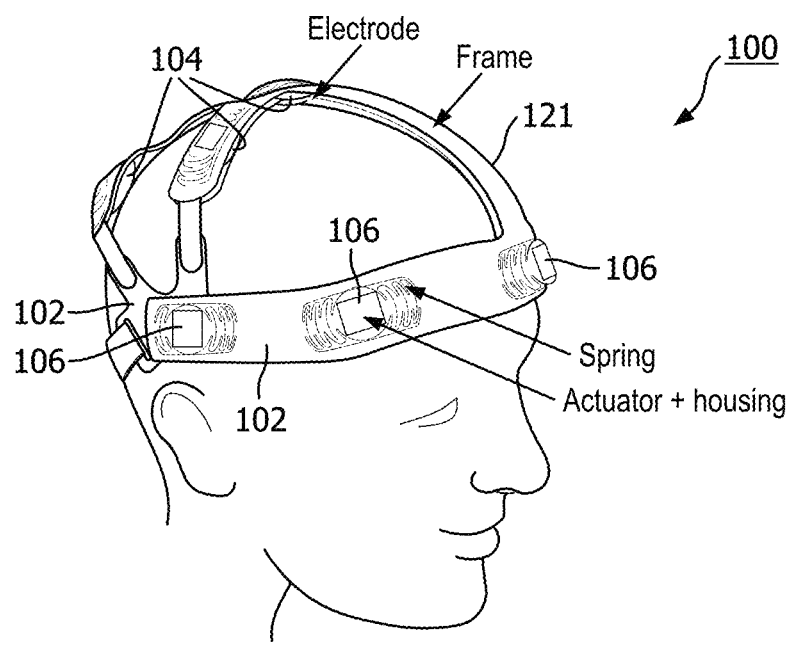
FIG. 3 illustrates an exemplary EEG system in accordance with an embodiment of the present patent application.
Figure 4:
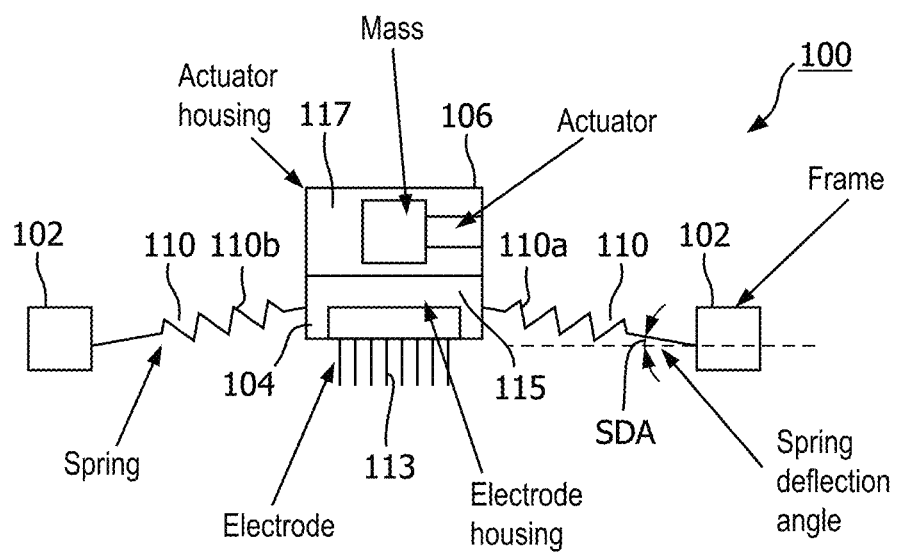
FIG. 4 illustrates another exemplary EEG system, where some components of the EEG system are not shown for sake of clarity, in accordance with an embodiment of the present patent application.
Figure 5:
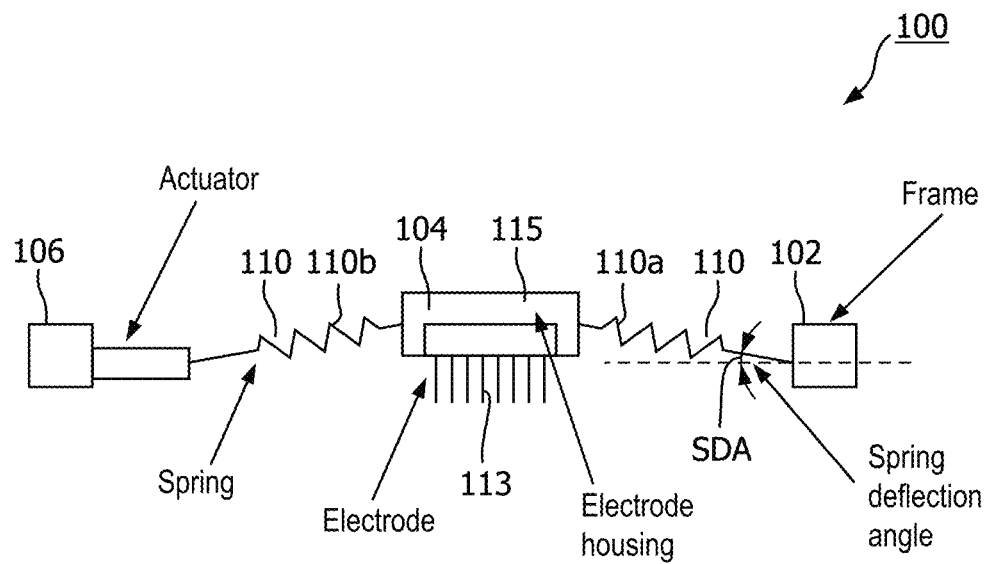
FIG. 5 illustrates another exemplary EEG system, where some components of the EEG system are not shown for sake of clarity, in accordance with an embodiment of the present patent application.

FIGS. 3-5 show exemplary dry EEG electrode systems 100 in accordance with embodiments of the present patent application.

In one embodiment, system 100 may further comprise a wearable device configured to be put at least partly around the head of a user. The wearable device includes support 102 configured for supporting electrodes 104. The wearable device may be integrated into a head band, head cap, headset, helmet, or the like. In one embodiment, dry EEG electrodes 104 with pins 113 are arranged on support 102. In one embodiment, support 102 may be deformable or a textile-like material. Support 102 may be used to integrate pin-structured electrodes 104 in the wearable device that can be placed on a user's head, such that it covers the area of the brain from which the electrical signals should be obtained. Support 102 may enable system 100 to follow the curvature of the user's head. The material of support 102 may be configured to adapt to the curvature of a person's head. The material of support 102 may be configured to be modeled by the person using the EEG system such that it fits to his/her head. Support 102 may, for example, be in the form of a patch. The patch may be positioned on or around the head of the user using the wearable device (e.g. a head band, head cap, headset, helmet or the like). In another embodiment, wearable device may be in form of a head band. Depending on the exact usage case of the system or wearable device, support 102 may be positioned at different locations on the user's head. Wearable devices that may be used in the present patent application are described in detail, for example, in International Patent Application Nos.: WO2011055291 A1 and WO 2013038285 A1. These two patent applications are incorporated in their entirety by reference herein.

In one embodiment, each EEG electrode 104 is configured to provide an impedance signal comprising at least one impedance value. In one embodiment, the impedance signal may comprise the respective impedance values over time.

In one embodiment, each EEG electrode 104 comprises a plurality of pins 113 for contacting the skin of the user. In this way, the comfort level of EEG system 100 and the convenience for the user may be improved. Pins 113 are configured to extend from an electrode housing 115 as shown in FIGS. 4 and 5. Pins 113 are configured to extend through the hair of the user when electrode 104 is positioned to be in contact with the user's scalp. The convenience and the comfort may be improved by designing electrode 104 in such a way that it has many degrees of freedom with respect to positioning electrode 104 and mounting it on the user's head.

In one embodiment, pins 113 may, for example, have rounded tips for contacting the skin. This further increases user comfort. In another embodiment, pins 113 may be arranged on a flexible substrate such that pins 113 flex and bend to ensure that the large number of pins 113 make galvanic contact to the skin. In yet another embodiment, electrodes 104 are attached to a flexible or deformable material. For example, the flexible or deformable material may be a textile-like material. In one embodiment, electrode 104 or pins 113 may be made of conductive metal or metal-alloy (e.g., silver, silver-chloride, or gold). In one embodiment, each electrode 104 may include a ball-and-socket joint. For example, this configuration introduces another layer of flexibility that can further improve balance of the electrode-skin contact impedances.

In one embodiment, the present patent application includes two mechanical elements that contribute to an optimal contacting system. These mechanical elements include spring mount 110 and actuator 106.

In one embodiment, individual electrodes 104 are mounted on lateral spring mount 110, and are capable of delivering sufficient contact pressure on the user's head/scalp as well as allowing some degree of decoupling of the (perpendicular and lateral) movement of individual electrode 104 with respect to headset frame or support 102. The partial mechanical decoupling via relatively compliant springs 110a, 110b allows for movements of the individual electrode 104, without exerting large forces on the headset frame 102. In this way, frame 102 stays in position while one individual electrode 104 can be repositioned while other individual electrodes 104 on the same headset frame 102 do not move.

In one embodiment, spring mount 110 is configured for applying a (nearly) constant axial force (along the axial direction/dimension) of electrode 104 on the user's scalp surface while having a selected spring stiffness in a lateral direction/dimension.

Lateral actuator 106 is configured to provide a lateral force (along the lateral direction/dimension) that is higher than a static friction force between electrode 104 and the user's scalp. In one embodiment, actuator 106 may be electromagnetic actuator (such as linear resonant actuator), piezoelectric vibration actuator or smart materials actuator such as shape memory alloy or electro-active polymer actuator. In one embodiment, actuator 106 is a mass spring system that vibrates, exerting a dynamic force on the user's scalp by the tips of electrode 104. The dynamic force is higher than the static friction force of electrode 104 on the scalp ($F_d = \mu F_n$, where $\mu$ is the friction coefficient and $F_n$ is the normal/static force). In one embodiment, for rubber dry electrodes, the skin friction coefficient is normally 2.4 and normal force is typically in the range of 10-20 grams for a comfortably fitting headset. In one embodiment, actuator 106 is configured for providing a force of higher than 0.5 N in the lateral direction/dimension. In one embodiment, typical linear resonant actuator (LRA) is capable of delivering such forces.

Actuator 106 is configured to create movement of its corresponding (individual) electrode 104. As shown in FIG. 4, actuator 106 is positioned on the back/top side of dry electrode 104. That is, an actuator housing 117 of actuator 106 is positioned on and attached to a side of electrode 104 that is opposite to the side of electrode 104 having pins 113 thereon. With the configuration of electrode 104 and actuator 106 as shown in FIG. 4, electrode 104 is configured to be actuated individually by vibrating electrode 104 in the mount or support 102. As shown in FIG. 4, springs 110a, 110b are configured to connect electrode 104 (and actuator 106 connected thereto) to support 102 on both sides of electrode 104/actuator 106.

In FIG. 5, actuator 106 is not directly attached or connected to electrode 104 (and its electrode housing 115). Rather, actuator 106, in FIG. 5, is spaced apart from and connected to electrode 104 (and its electrode housing 115) via spring member 110b. As shown in FIG. 5, spring 110a is configured to connect electrode 104 to support 102 on one side of electrode 104, while spring 110b is configured to connect electrode 104 to actuator 106 on the other side of electrode 104. In one embodiment, as shown in FIG. 5, actuator 106 is attached to spring 110b and moves electrode 104 in the lateral direction/dimension by retracting, thereby pulling on spring 110b and repositioning electrode 104. The retracting electrode creates a force imbalance between the two springs, generating a lateral force on the electrode-scalp contact. When the force is high enough to overcome the friction of the electrode pins on the scalp, the electrode repositions itself and the force balance between the springs will be restored.

Springs 110a, 110b being used in spring mount 110 are typically flat springs that have a low stiffness in the lateral direction/dimension. Hence, spring 110a, 110b of spring mount 110 can deform in the axial direction/dimension also. In one embodiment, the axial force (along the axial direction/dimension) of electrode 104 on the user's scalp surface is dependent on the spring deflection angle, SDA (as shown in FIGS. 4 and 5). Spring deflection angle, SDA is the angle between the lateral spring 110a/11b and frame 102 (i.e., support/frame 102 is parallel to the user's scalp surface). For small spring deflection angles (SDAs), the force does not change much with an increasing angle. The force is relatively independent of (small) deformations on the axial direction/dimension, creating an almost equal pressure distribution across all electrode locations.

Figure 6:
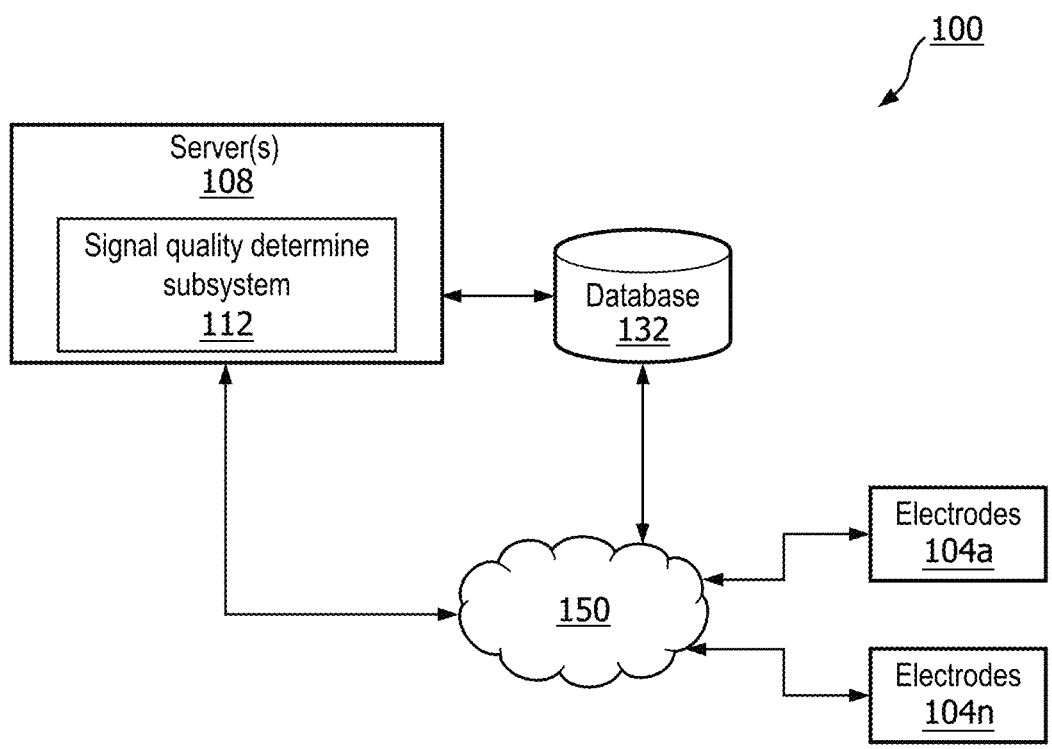
FIG. 6 illustrates another exemplary EEG system, where some components of the EEG system are not shown for sake of clarity, in accordance with another embodiment of the present patent application.

As shown in FIG. 6, system 100 for obtaining electroencephalography (EEG) signals from one or more dry electroencephalography (EEG) electrodes may comprise server 108 (or multiple servers 108). Server 108 may comprise signal quality determination subsystem 112, or other components or subsystems. In one embodiment, computer system (e.g., comprising server 108) obtains impedance signal information and EEG signal information from electrodes 104.

In one embodiment, the impedance signal information generally refers to impedance signal comprising at least one impedance value of electrode 104 with respect to the skin. In one embodiment, the EEG signal information generally refers to EEG signal. In one embodiment, electrodes 104 may be configured to provide other physiological signal including, but not limited to an ECG, EMG, EOG or GSR signal.

In one embodiment, the impedance signal information and the EEG signal information may be obtained from database 132 that is being updated in real-time by one or more electrodes 104. In one scenario, one or more electrodes 104 may provide the impedance signal information and the EEG signal information to a computer system (e.g., comprising server 108) over a network (e.g., network 150) for processing.

In one embodiment, signal quality determination subsystem 112 determines signal quality of the corresponding electrode 104 from its impedance signal information from electrode 104.

In one embodiment, system 100 is configured to determine the signal quality of the electrode signals. The procedure of determining the signal quality of the electrode signals using impedance value from electrode 104 is described in detail, for example, in International Patent Application No.: WO 2013038285 A1, which is incorporated in its entirety by reference herein. For example, the signal quality of each electrode 104 may be assessed by an impedance value measurement. As described in International Patent Application No. WO2013038285A1, this can be done by processing of the EEG data to extract signal quality from features in the EEG. This can occur embedded via the EEG signal or remotely via analysis of the EEG signal and algorithms, which determine the signal quality from the EEG data.

Figure 9:
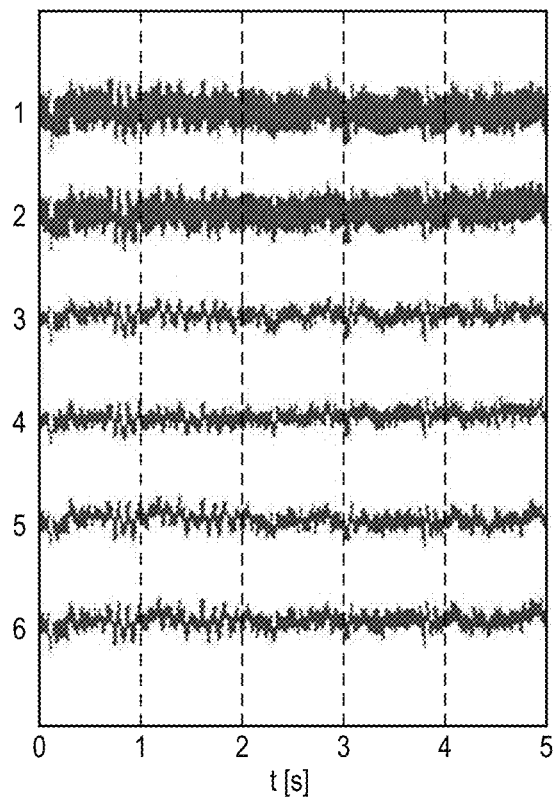
FIGS. 9 and 10 show graphs of electrode impedance values at several electrode positions over time from the EEG electrode headset.

In one embodiment, algorithms used to determine the signal quality of the EEG electrode may include algorithms based on (relative) signal amplitude. For example, poor quality signals generally have a higher signal amplitude and increased mains noise. An algorithm to determine the signal quality may, therefore, be based on the relative signal amplitude, before or after filtering the mains noise. The mains noise is a good absolute measure for the quality of the contact of electrode 104 with the user's scalp as high impedance contacts cause increased pickup from mains disturbance. For example, referring to FIG. 9, signal 1 has the poor/lowest contact quality, while signal 6 has the highest contact quality.

For instance, in one embodiment, the headset may be calibrated using high quality (wet) electrodes before leaving the factory/manufacturer. If, in use the signal amplitude at the mains frequency is higher than (for instance, 5 times the calibration value for any or all electrodes), then system 100 for increasing the contact quality is activated. In one embodiment, an universal reference noise (or amplitude) level may be programmed as a reference level (i.e., relating to an impedance threshold) to compare the noise level to and determine whether any adjustments are needed for each actuator.

Figure 10:
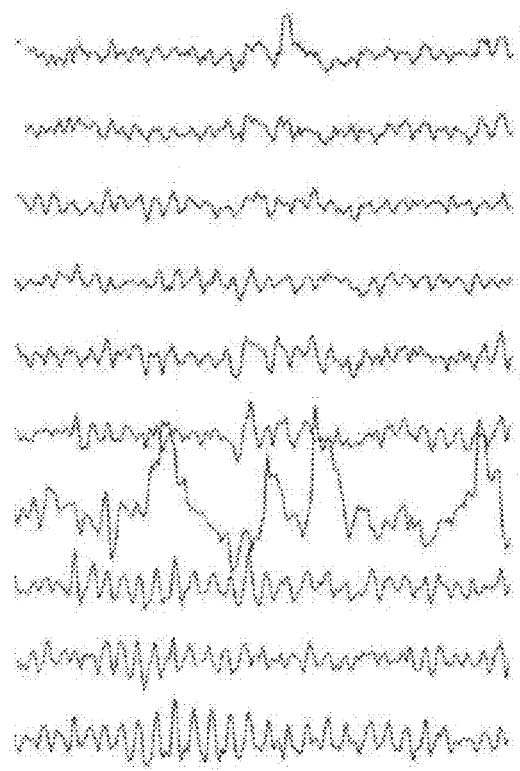

In one embodiment, the filtered amplitude is typically best to determine relative differences in contact quality between electrodes 104. For example, if the filtered amplitude of electrode 104 is above a certain relative threshold compared to the amplitude of other signals, then respective electrode 104 may be adjusted by system 100. For example, such a threshold may be set at two to five the amplitude as shown in FIG. 10. As shown in FIG. 10, the electrode P3 has bad contact quality.

In one embodiment, a finer threshold may be determined by programming a typical distribution of signal amplitudes (i.e., due to variations in EEG strength across the scalp) and determining any discrepancies of the actual signal amplitudes compared to the ideal distribution. In one embodiment, a more robust quality determining mechanism may be based on both methods. That is, in one embodiment, the raw (unfiltered) signal is used as an absolute (coarse) measurement system addressing all electrodes while the filtered signal is used to determine relative differences in the signal amplitude. In one embodiment, when a poor signal (or high impedance) is detected, actuator 106 causes a lateral movement, repositioning electrode 104 and creating a chance for better contact that can again be measured by system 100.

Figure 8:
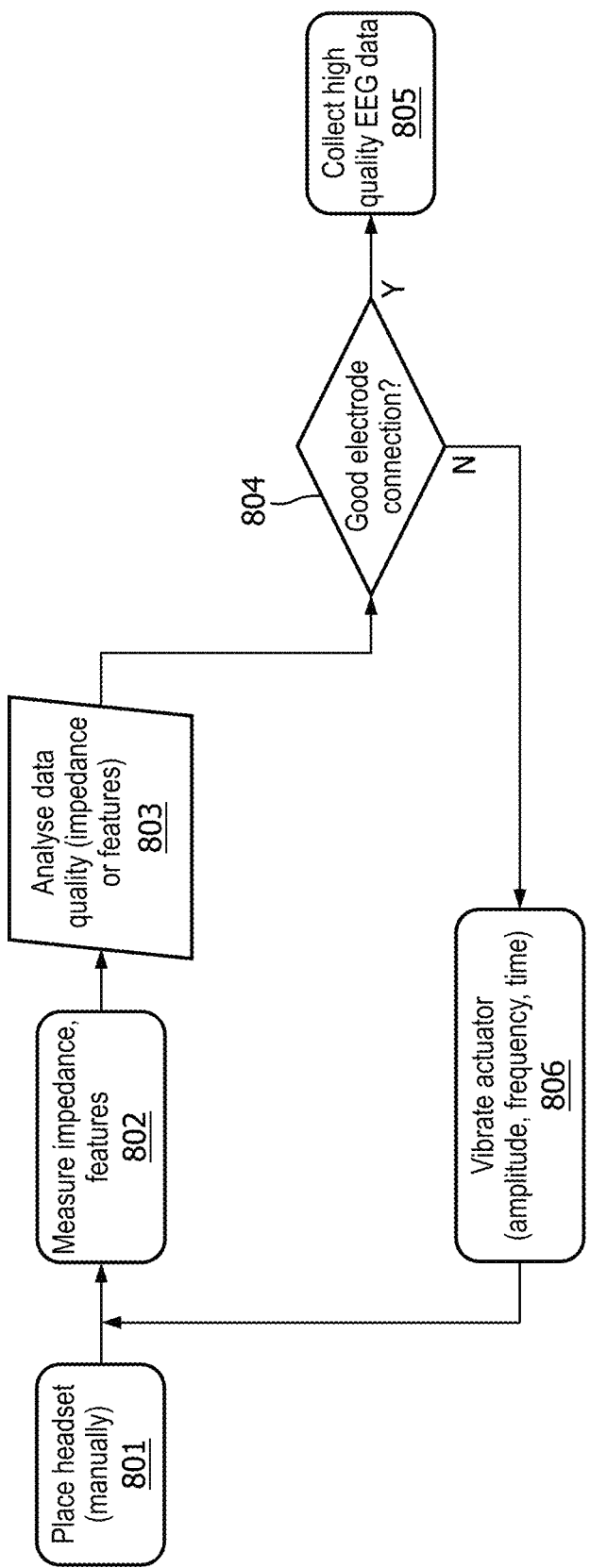
FIG. 8 shows another exemplary method for automatically repositioning EEG electrodes of the exemplary EEG system in accordance with an embodiment of the present patent application.

When system 100 senses a low/poor quality electrode signal, system 100 is configured to activate actuator 106 associated with the faulty connected electrode 104. The vibration or movement of electrode 104, by actuator 106, changes the connection of electrode 104 with the skin. System 100 again measures the signal quality. This process is repeated until a high quality connection is detected. For example, these procedural steps are depicted in FIG. 8. For example, at procedure 801, EEG headset is manually placed on the user's head/scalp. At procedure 802, impedance signal information is obtained from each of the electrodes 104 positioned on the headset. At procedures 803 and 804, the obtained impedance signal information is analyzed to determine whether each of the electrodes 104 have good signal quality (and good contact with the user's scalp). If yes, at procedure 805, EEG data is obtained from all electrodes 104 having good signal quality (and good contact with the user's scalp). If not, at procedure 806, actuator 106 corresponding to electrode 104 that has a poor signal quality is actuated to move that electrode 104 in at least two dimensions, including the axial dimension and the lateral dimension to enable that EEG electrode 104 to contact the skin at a different position. That is, system 100 is further configured to actuate actuator 106 based on the determination of poor signal quality. In one embodiment, one or more actuators 106 corresponding to one or more electrodes 104 that have poor signal quality are actuated simultaneously to move corresponding one or more electrodes 104 in at least two dimensions.

In one embodiment, signal quality determination subsystem 112 is configured to determine signal quality continuously or repeatedly. For example, the determination can be done in real-time or at predefined time intervals. In this way, it can be ensured that the impedances or the equality relation of the impedances is preserved over time. This can in particular be achieved by continuous or repeated readjustment of the all electrodes, while the system is in use. The readjustment can keep the impedances within the desired boundaries/impedance range.

In one embodiment, system 100 may further comprise an EEG signal processing system for processing the EEG signal of electrode 104. Alternatively, system 100 may further comprise a transmission link for transmitting the EEG signals to an external device or system for further processing and analysis. In one embodiment, one or more of the above mentioned subsystems can be implemented in the same processing unit (e.g., processor or microprocessor), or can be implemented in separate processing units.

Figure 7:
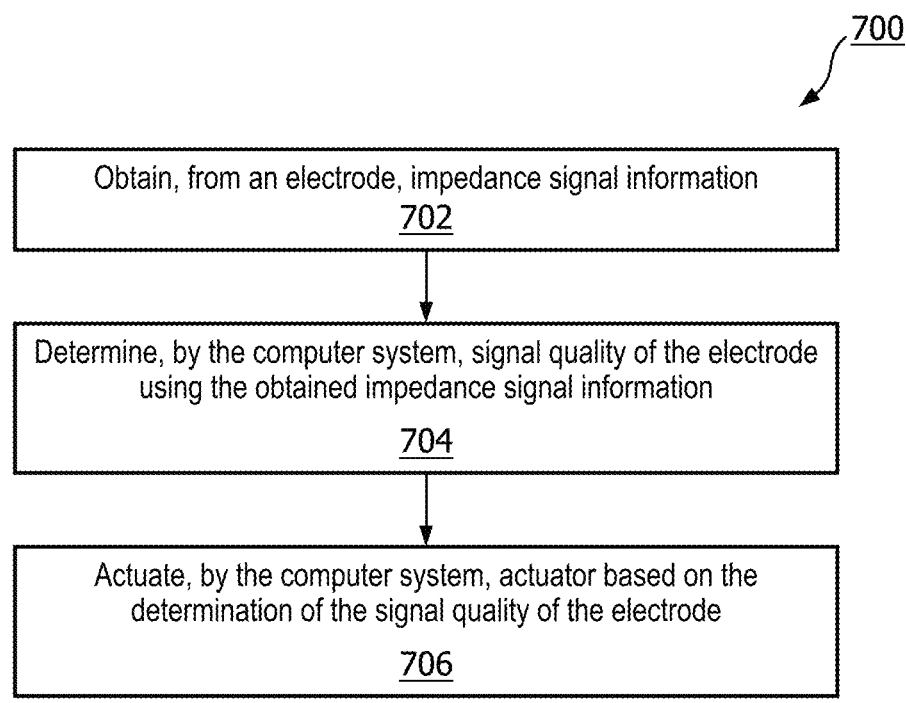
FIG. 7 shows an exemplary method for automatically repositioning dry EEG electrodes of the exemplary EEG system in accordance with an embodiment of the present patent application.

Referring to FIG. 7, an exemplary method 700 for obtaining signals from one or more dry electroencephalography (EEG) electrodes is provided. Method 700 is implemented by computer system 108 that comprises one or more physical processors 108 executing computer program instructions which, when executed, perform method 700. Method 700 includes obtaining, from electrode 104, impedance signal information at procedure 702; and actuating, by computer system 108, actuator 106 to move the EEG electrode based on a comparison of the obtained impedance signal with an impedance threshold at procedure 706. Method 700 also includes determining, by computer system 108, signal quality of electrode 104 using the impedance value information at procedure 704 and actuating, by computer system 108, actuator 106 to move the EEG electrode based on the determination.

In one embodiment, the various computers and subsystems illustrated in FIG. 6 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in system 100. As such, the processors may include one or more of a digital processor, an analog processor, or a digital circuit designed to process information, an analog circuit designed to process information, a state machine, and/or other mechanisms for electronically processing information. In one embodiment, the processors may include a plurality of processing units. These processing units may be physically located within the same device, or the processors may represent processing functionality of a plurality of devices operating in coordination. The processors may be programmed to execute computer program instructions to perform functions described herein of subsystem 112 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the subsystem 112 described herein is for illustrative purposes, and is not intended to be limiting, as subsystem 112 may provide more or less functionality than is described. As another example, additional subsystems may be programmed to perform some or all of the functionality attributed herein to subsystem 112.

The system and method of the present patent application may be applied in the area of brain signal acquisition systems used in the clinical and consumer domain. They range from practical headset designs for EEG measurements, to clinically designed headsets for EEG patient monitoring in hospitals, sleep centers or at home. The clinical relevance can be seen in the areas of post-surgical recovery monitoring and rehabilitation and in providing alternative or complementary communication and/or control channels. The commercial value of the applications in the consumer arena is in the area of Neurofeedback for improving cognition and enhancing relaxation, in the area of prevention and monitoring of mental health, and in gaming market, especially in games that include BCI technology.

An important application for convenient brain wave sensing technology is Alpha Neurofeedback. Alpha Neurofeedback (NF) is a novel method which may find application areas both in consumer and professional healthcare products. NF induces a feeling of ease in a person without the person feeling the burden of responsibility for his own mental state. This is particularly relevant for a hospital setting, where the user, or patient, is put at ease in a very subtle way without requiring them to be aware of the effect of NF. This is important for a hospital setting as it means the patient is not burdened with the feeling of being responsibly of having to relax. Any such burden, especially when coupled to the quality of for example a MR or PET scan, can be counterproductive and often induces stress rather than reducing it.

In the clinical domain the usage of Alpha Neurofeedback can provide natural and relaxing experience, e.g., to stressed individuals or to patients in the uptake procedure for PET scans. As the NF setup requires the usage of electrodes the proposed patent application can help in developing a convenient setup that would not impose additional burden to the patients. The solution can be realized either as a specially designed headset or be integrated in the chair (armchair) where the patient sits or lays down before the clinical procedure. In the later, the complete setup should be integrated in the chair where a person positions the back of his head.

The system and method of the present patent application may also be used for sleep monitoring devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. An electroencephalography (EEG) system comprising:
a support configured to be positioned at least partially around the head of a user;
an EEG electrode configured to be supported by the support and to be positioned for contacting skin of the user;
an actuator operatively coupled to the EEG electrode, the actuator configured to move the EEG electrode in at least two dimensions, including an axial dimension and a lateral dimension to enable the EEG electrode to contact the skin at different locations;
a spring structure including a first spring having a first end coupled to a first side of the EEG electrode and a second end coupled to the support and a second spring having a first end coupled to a second side of the EEG electrode and a second end coupled to the support, wherein the first side of the EEG electrode and the second side of the EEG electrode are opposite of each other, and wherein the spring structure is configured to deliver contact pressure of the EEG electrode on the user's head and to allow decoupling of the movement, in the axial dimension and in the lateral dimension, of the EEG electrode with respect to the support; and
one or more physical processors operatively connected with the EEG electrode and the actuator, the one or more physical processors being programmed with computer program instructions which, when executed cause the one or more physical processors to:
obtain an impedance signal from the EEG electrode; and
actuate the actuator to move the EEG electrode based on a comparison of the obtained impedance signal with an impedance threshold,
wherein the actuator is disposed on a side of the EEG electrode opposite the head of the user, wherein the actuator is structured to vibrate to generate a force of at least 0.5N on the EEG electrode in the lateral dimension, the force being higher than a static friction force of the EEG electrode on a scalp of the user, and wherein actuation of the actuator to move the EEG electrode includes causing the actuator to vibrate.

2. The system of claim 1, wherein the spring structure is configured to enable a constant axial force of the EEG electrode to be applied on the user's head and to provide a predetermined spring stiffness in the lateral dimension.

3. The system of claim 1, wherein the actuator is positioned in an actuator housing and the EEG electrode is positioned in an electrode housing, wherein the actuator housing is attached to the electrode housing.

4. A method for obtaining signals from one or more dry electroencephalography (EEG) electrodes of an EEG headset, the EEG headset being configured to be positioned at least partially around the head of a user, the method being implemented by a computer system that comprises one or more physical processors executing computer program instructions which, when executed, perform the method, the method comprising:
obtaining, from an EEG electrode, impedance signal information, the EEG electrode being configured to be positioned for contacting skin of the user; and
actuating, by the computer system, an actuator to move the EEG electrode in at least two dimensions, including an axial dimension and a lateral dimension to enable the EEG electrode to contact the skin at different locations based on a comparison of the obtained impedance signal information with an impedance threshold, the EEG electrode and the actuator being operatively connected with the computer system,
wherein the actuator is disposed on a side of the EEG electrode opposite the head of the user, wherein the actuator is structured to vibrate, wherein actuation of the actuator to move the EEG electrode includes causing the actuator to vibrate to generate a force of at least 0.5N on the EEG electrode in the lateral dimension, the force being higher than a static friction force of the EEG electrode on a scalp of the user, wherein the EEG headset include a support configured to be positioned at least partially around the head of a user and a spring structure including a first spring having a first end coupled to a first side of the EEG electrode and a second end coupled to the support and a second spring having a first end coupled to a second side of the EEG electrode and a second end coupled to the support, wherein the first side of the EEG electrode and the second side of the EEG electrode are opposite of each other, and wherein the spring structure is configured to deliver contact pressure of the EEG electrode on the user's head and to allow decoupling of the movement, in the axial dimension and in the lateral dimension, of the EEG electrode with respect to the support.

5. The method of claim 4, wherein the axial dimension extends along a plane that is perpendicular to the user's head and is perpendicular to the lateral dimension.

6. The method of claim 4, wherein the lateral dimension extends along a plane that is parallel to the user's head and is perpendicular to the axial dimension.

7. The method of claim 4, wherein the impedance threshold is 10MΩ.

8. A system for obtaining electroencephalography (EEG) signals comprising:
   electrode means for contacting the skin of the user;
   means for supporting the electrode means on the head of a user;
   means for moving the electrode means in at least two dimensions, including an axial dimension and a lateral dimension to enable the electrode means to contact the skin at different locations;
   a spring structure including a first spring having a first end coupled to a first side of the electrode means and a second end coupled to the means for supporting and a second spring having a first end coupled to a second side of the electrode means and a second end coupled to the means for supporting, wherein the first side of the electrode means and the second side of the electrode means are opposite of each other, and wherein the spring structure is configured to deliver contact pressure of the electrode means on the user and to allow decoupling of the movement, in the axial dimension and in the lateral dimension, of the electrode means with respect to the means for supporting; and
   means for executing machine-readable instructions with at least one processor, wherein the machine-readable instructions comprising:
      obtaining, from the electrode means, impedance signal information, the electrode means being configured to be positioned for contacting skin of the user; and
      actuating the means for moving to move the electrode means in at least two dimensions, including an axial dimension and a lateral dimension to enable the electrode to contact the skin at different locations based on a comparison of the obtained impedance signal information with an impedance threshold, the electrode means and the means for moving being operatively connected with the means for executing,
   wherein the means for moving is disposed on a side of the electrode means opposite the head of the user, wherein the means for moving is structured to vibrate to generate a force of at least 0.5N on the EEG electrode in the lateral dimension, the force being higher than a static friction force of the EEG electrode on a scalp of the user, and wherein actuation of the means for moving to move the electrode means includes causing the means for moving to vibrate.

9. The system of claim 8, wherein the axial dimension extends along a plane that is perpendicular to the user's head and is perpendicular to the lateral dimension.

10. The system of claim 8, wherein the lateral dimension extends along a plane that is parallel to the user's head and is perpendicular to the axial dimension.

11. The system of claim 8, wherein the impedance threshold is 10MΩ.

* * * * *